(12) United States Patent
Lee et al.

(10) Patent No.: US 9,428,774 B2
(45) Date of Patent: *Aug. 30, 2016

(54) ENGINEERED MICROORGANISM PRODUCING HOMO-SUCCINIC ACID AND METHOD FOR PREPARING SUCCINIC ACID USING THE SAME

(71) Applicant: Korea Advanced Institute of Science and Technology, Daejeon (KR)

(72) Inventors: Sang Yup Lee, Daejeon (KR); Sung Won Lim, Seoul (KR); Hyohak Song, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/874,385

(22) Filed: Oct. 3, 2015

(65) Prior Publication Data

US 2016/0017383 A1 Jan. 21, 2016

Related U.S. Application Data

(63) Continuation of application No. 12/359,322, filed on Jan. 25, 2009, now Pat. No. 9,217,138, which is a continuation-in-part of application No. PCT/KR2007/003574, filed on Jul. 25, 2007.

(30) Foreign Application Priority Data

Jul. 28, 2006 (KR) .................. 10-2006-0071666

(51) Int. Cl.
*C12P 7/46* (2006.01)
*C12N 1/20* (2006.01)
(Continued)

(52) U.S. Cl.
CPC . *C12P 7/46* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS 5,143,833 A 9/1992 Datta
5,143,834 A 9/1992 Glassner et al.
(Continued)

FOREIGN PATENT DOCUMENTS

CA 2621562 A1 3/2007
JP 11-206385 A 8/1999
(Continued)

OTHER PUBLICATIONS

McKinlay, J., et al., "Insights into Actinobacillus succinogenes Fermentative Metabolism in a Chemically Defined Growth Medium", "Appl. Environ. Microbiol.", Nov. 2005, pp. 6651-6656, vol. 71, No. 11.

(Continued)

*Primary Examiner* — Robert Mondesi
*Assistant Examiner* — Richard Ekstrom
(74) *Attorney, Agent, or Firm* — Hultquist, PLLC; Steven J. Hultquist

(57) ABSTRACT

The present invention relates to a mutant microorganism, which is selected from the group consisting of genus *Mannheimia*, genus *Actinobacillus* and genus *Anaerobiospirillum*, producing homo-succinic acid and a method for producing homo-succinic acid using the same, and more particularly to a mutant microorganism producing succinic acid at a high concentration while producing little or no other organic acids in anaerobic conditions, which is obtained by disrupting a gene encoding lactate dehydrogenase (ldhA), a gene encoding phosphotransacetylase (pta), and a gene encoding acetate kinase (ackA), without disrupting a gene encoding pyruvate formate lyase (pfl), as well as a method for producing succinic acid using the same. The inventive mutant microorganism has the property of having a high growth rate and succinic acid productivity while producing little or no organic acids, as compared to the prior strains producing succinic acid. Thus, the inventive mutant microorganism is useful to produce succinic acid for industrial use.

4 Claims, 6 Drawing Sheets

(51) Int. Cl.
  *C12N 15/90* (2006.01)
  *C12N 9/04* (2006.01)
  *C12N 9/10* (2006.01)
  *C12N 9/12* (2006.01)

(52) U.S. Cl.
  CPC ......... *C12N 9/1029* (2013.01); *C12N 9/1217* (2013.01); *C12N 15/902* (2013.01); *C12Y 203/01054* (2013.01); *Y02P 20/52* (2015.11)

(56) References Cited

U.S. PATENT DOCUMENTS

| | | |
|---|---|---|
| 5,168,055 A | 12/1992 | Datta et al. |
| 5,504,004 A | 4/1996 | Guettler et al. |
| 5,521,075 A | 5/1996 | Guettler et al. |
| 5,573,931 A | 11/1996 | Guettler et al. |
| 5,604,177 A | 2/1997 | Kinnersley et al. |
| 5,770,435 A | 6/1998 | Donnelly et al. |
| 6,159,738 A | 12/2000 | Donnelly et al. |
| 7,241,594 B2 | 7/2007 | Lee et al. |
| 7,351,578 B2 | 4/2008 | Cheo et al. |
| 7,393,632 B2 | 7/2008 | Cheo et al. |
| 7,470,530 B2 | 12/2008 | Lee et al. |
| 7,470,770 B2 | 12/2008 | Lee et al. |
| 7,588,934 B2 | 9/2009 | Lee |
| 7,803,587 B2 | 9/2010 | Lee |
| 8,691,516 B2 | 4/2014 | Lee et al. |
| 9,217,138 B2 * | 12/2015 | Lee ..................... C12N 9/1217 |
| 2006/0046288 A1 | 3/2006 | Ka-Yiu et al. |
| 2006/0073577 A1 | 4/2006 | Ka-Yiu et al. |
| 2006/0141594 A1 | 6/2006 | San et al. |
| 2007/0111294 A1 | 5/2007 | Burgard et al. |
| 2009/0203095 A1 | 8/2009 | Lee et al. |
| 2011/0008851 A1 | 1/2011 | Scholten et al. |

FOREIGN PATENT DOCUMENTS

| | | |
|---|---|---|
| KR | 10-0267505 B1 | 7/2000 |
| KR | 10-0372218 B1 | 1/2003 |
| KR | 10-2010-0070327 A | 6/2010 |
| WO | 9716528 A1 | 5/1997 |
| WO | 0200846 A1 | 1/2002 |
| WO | 2005052135 A1 | 6/2005 |
| WO | 2006031424 A2 | 3/2006 |
| WO | 2007030830 A2 | 3/2007 |
| WO | 2009024294 A1 | 2/2009 |

OTHER PUBLICATIONS

McKinlay, J., et al., "Prospects for a bio-based succinate industry", "Appl. Microbiol. Biotechnol.", Jul. 4, 2007, pp. 727-740, vol. 76.

Millard, C., et al., "Enhanced production of succinic acid by overexpression of phosphoenolpyruvate carboxylase in *Escherichia coli*", "Appl. Environ. Microbiol.", May 1996, pp. 1808-1810, vol. 62, No. 5.

Miller-Klein Associates, "Use of Tallow in Biodiesel", Oct. 2006, pp. 1-3.

Hong, S., et al., "NCBI Protein Locus No. AAU37367: FumC protein [Mannheimia succiniciproducens MBEL55E]", Oct. 2004, pp. 1-2.

Ng, W., et al., "Genome sequence of *Halobacterium* species NRC-1", "Proc. Natl. Acad. Sci. USA", Oct. 24, 2000, pp. 12176-12181, vol. 97, No. 22.

Ng, W., et al., "Genome sequence of *Halobacterium* species NRC-1: Supplemental Figure 2: Genetic map of the *Halobacterium* NRC-1 chromosome (2,014,239 bp) and two minichromosomes, pNRC200 (365,425 bp) and pNRC100 (191,346 bp)", "Proc. Natl. Acad. Sci. USA", Oct. 24, 2000, pp. 1-4, vol. 97, No. 22.

Ng, W., et al., "Genome sequence of *Halobacterium* species NRC-1: Supplemental Table 2: *Halobacterium* NRC-1 genes and genetic elements", "Proc. Natl. Acad. Sci. USA", Oct. 24, 2000, pp. 1-4, vol. 97, No. 22.

Nierman, W. et al., "Complete genome sequence of *Caulobacter crescentus*", "Proc. Natl. Acad. Sci. USA", Mar. 20, 2001, pp. 4136-4141, vol. 98, No. 7.

Nierman, W., et al., "Fig. 4. Linear representation of the *Caulobacter crescentus* genome", "Proc. Natl. Acad. Sci. USA", Mar. 20, 2001, vol. 98, No. 7.

Perna, N., et al., "Genome sequence of enterohaemorrhagic *Escherichia coli* O157:H7", "Nature", Jan. 25, 2001, pp. 529-533, vol. 409, No. 6819.

Pettigrew, D., et al., "A Single Amino Acid Change in *Escherichia coli* Glycerol Kinase Abolishes Glucose Control of Glycerol Utilization In Vivo", "J. Bacteriol.", May 1996, pp. 2846-2852, vol. 178, No. 10.

Phue, J., et al., "Glucose Metabolism at High Density Growth of *E. coli* B and *E. coli* K: Differences in Metabolic Pathways Are Responsible for Efficient Glucose Utilization in *E. coli* B as Determined by Microarrays and Northern Blot Analyses", "Biotechnology and Bioengineering", Jun. 30, 2005, pp. 805-820, vol. 90, No. 7.

Popov, V., et al., "NAD+-dependent formate dehydrogenase", "Biochem. J.", 1994, pp. 625-643, vol. 301, No. 2.

Qian, Z. et al., "Metabolic Engineering of *Escherichia coli* for the Production of Putrescine: A Four Carbon Diamine", "Biotechnol. Bioeng.", Aug. 27, 2009, pp. 651-662, vol. 104, No. 4.

Rizzino, A., et al., "Growth of Embryonal Carcinoma Cells in Serum-Free Medium", "Proc. Natl. Acad. Sci. USA", Apr. 1, 1978, pp. 1844-1848, vol. 75, No. 4.

Rochelle, P., et al., "DNA extraction for 16A rRNA gene analysis to dtermine genetic diversity in deep sediment communities", "FEMS Microbiology Letters", 1992, pp. 59-66, vol. 100.

Ruepp, A., et al., "The genome sequence of the thermoacidophilic scavenger Thermoplasma acidophilum", "Nature", Sep. 28, 2000, pp. 508-513, vol. 407, No. 6803.

Samuelov, N., et al., "Influence of CO2—HCO3-Levels and pH on Growth, Succinate Production, and Enzyme Activities of Anaerobiospirillum succiniciproducens", "Appl. Environ. Microbiol.", Oct. 1991, pp. 3013-3019, vol. 57, No. 10.

Samuelov, N., et al., "Whey Fermentation by Anaerobiospirillum succiniciproducens for Production of a Succinate-Based Animal Feed Additive", "Applied and Environmental Microbiology", May 1999, pp. 2260-2263, vol. 65, No. 5.

Schaefer, A., et al., "Small mobilizable multi-purpose cloning vectors derived from the *Escherichia coli* plasmids pK18 and pK19: selection of defined deletions in the chromosome of Corynebacterium glutamicum", "Gene", 1994, pp. 69-73, vol. 145.

Schneider, J., et al., "Putrescine production by engineered Corynebacterium glutamicum", "Appl Microbiol Biotechnol", Jul. 27, 2010, pp. 859-868, vol. 88.

Scholten, E., et al., "Succinic acid production by a newly isolated bacterium", "Biotechnol Lett", Jul. 24, 2008, pp. 2143-2146, vol. 30.

"Score Search results AE016827 in U.S. Appl. No. 11/228,927", Downloaded on Jul. 6, 2006 from http://es/ScoreAccessWeb/GetItem.action?Appld=11228927&seqld=542104&ItemName=us-11-228-927.

Song, H., et al., "Production of succinic acid by bacterial fermentation", "Enzyme and Microbial Technology", Jul. 2006, pp. 352-361, vol. 39.

Steinmetz, M., et al., "Plasmids designed to alter the antibiotic resistance expressed by insertion mutation in Bacillus subtilis, through in vivo recombination", "Gene", 1994, pp. 79-83, vol. 142.

"STIC Search Report—us-11-229-368-3.rge", Sep. 13, 2007, pp. 1-5.

"STIC Search Report—us-11-229-368-4.rup", Sep. 13, 2007, pp. 1-4.

"STIC Search Report, us-11-228-945-7.rup", Apr. 14, 2006, p. 1.

"STIC Search Report, us-11-228-945-8.rup", Apr. 14, 2006, pp. 1-2.

Stols, L., et al., "Production of succinic acid through overexpression of NAD(+)-dependent malic enzyme in an *Escherichia coli* mutant", "Appl. Environ. Microbiol.", Jul. 1997, pp. 2695-2701, vol. 63, No. 7.

Teusink, B., et al., "In Silico Reconstruction of the Metabolic Pathways of Lactobacillus plantarum: Comparing Predictions of

(56) References Cited

OTHER PUBLICATIONS

Nutrient Requirements with Those from Growth Experiments", "Appl. Environ. Microbiol.", Nov. 2005, pp. 7253-7262, vol. 71, No. 11.

Urbance, S., et al., "Evaluation of succinic acid continuous and repeat-batch biofilm fermentation by Actinobacillus succinogenes using plastic composite support bioreactors", "Appl . . . Microbiol. Biotechnol.", Nov. 2004, pp. 664-670, vol. 65, No. 6.

Van Der Werf, M., et al., "Environmental and physiological factors affecting the succinate product ratio during carbohydrate fermentation by *Actinobacillus* sp. 130Z", "Arch. Microbiol.", Jun. 1997, pp. 332-342, vol. 167, No. 6.

Vemuri, G., et al., "Succinate production in dual-phase *Escherichia coli* fermentations depends on the time of transition from aerobic to anaerobic conditions", "J. Ind. Microbiol. Biotech.", Jun. 2002, pp. 325-332, vol. 28, No. 6.

Vemuri, G., et al., "Effects of Growth Mode and Pyruvate Carboxylase on Succinic Acid Production by Metabolically Engineered Strains of *Escherichia coli*", "Appl. Environ. Microbiol.", Apr. 2002, pp. 1715-1727, vol. 68, No. 4.

Willke, T., et al, "Industrial bioconversion of renewable resources as an alternative to conventional chemistry", "Appl. Microbiol. Biotechnol.", Dec. 2004, pp. 131-142, vol. 66, No. 2.

Wolfe, A., "The Acetate Switch", "Microbiology and Molecular Biology Reviews", Mar. 2005, pp. 12-50, vol. 69, No. 1.

Yazdani, S., et al., "Anaerobic fermentation of glycerol: a path to economic viability for the biofuels industry", "Current Opinion in Biotechnology", May 25, 2007, pp. 213-219, vol. 18.

Zeikus, J., "Chemical and fuel production by anaerobic bacteria", "Ann. Rev. Microbiol.", 1980, pp. 423-464, vol. 34.

Zeikus, J., et al., "Biotechnology of succinic acid production and markets for derived industrial products", "Appl. Microbiol. Biotechnol.", May 1999, pp. 545-552, vol. 51, No. 5.

Zhang, J., et al., "Chemically defined media for commercial fermentations", "Appl. Microbiol. Biotechnol.", Apr. 1999, pp. 407-421, vol. 51, No. 4.

Zwaig, N., et al., "Glycerol Kinase, the Pacemaker for the Dissimilation of Glycerol in *Escherichia coli*", "J. Bacteriol.", Jun. 1970, pp. 753-759, vol. 102, No. 3.

Jun. 4, 2015 Office Action issued in U.S. Appl. No. 12/359,322 by Richard C. Ekstrom.

Oct. 6, 2011 Office Action issued in U.S. Appl. No. 12/359,322 by Anne Marie Falk.

Oct. 8, 2014 Office Action issued in U.S. Appl. No. 12/359,322 by Richard C. Ekstrom.

Nov. 15, 2012 Office Action issued in U.S. Appl. No. 12/359,322 by Anne Marie Falk.

Adams, M., et al., "The Genome Sequence of *Drosophila melanogaster*", "Science", Mar. 24, 2000, pp. 2185-2195, vol. 287, No. 5461.

Ajinomoto Group, "Environmental Report 2003", 2003, p. 21.

Andersson, C., et al., "Effect of Different Carbon Sources on the Production of Succinic Acid Using Metabolically Engineered *Escherichia coli*", "Biotechnol. Prog.", Jan. 25, 2007, pp. 381-388, vol. 23.

Berrios-Rivera, S., et al., "Metabolic Engineering of *Escherichia coli*: Increase of NADH Availability by Overexpressing an NAD+-Dependent Formate Dehydrogenase", "Metab. Eng.", Jul. 2002, pp. 217-229, vol. 4, No. 3.

Chang, D., et al., "Homofermentative production of D- or L-lactate in metabolically engineered *Escherichia coli* RR1", "Applied and Environmental Microbiology", Apr. 1999, pp. 1384-1389, vol. 65, No. 4.

Chao, Y., et al., "Alteration of growth yield by overexpression of phosphoenolpyruvate carboxylase and phosphoenolpyruvate carboxykinase in *Escherichia coli*", "Appl. Environ. Microbiol.", Dec. 1993, pp. 4261-4265, vol. 59, No. 12.

Chatterjee, R., et al., "Mutation of the ptsG Gene Results in Increased Production of Succinate in Fermentation of Glucose by *Escherichia coli*", "Appl. Environ. Microbior.", Jan. 2001, pp. 148-154, vol. 67, No. 1.

Cocaign-Bousquet, M., et al., "Rational development of a simple synthetic medium for the sustained growth of Lactococcus lactis", "J. Appl. Bacteria", 1995, pp. 108-116, vol. 79.

Cowan, D., "Genomics: Use your neighbour's genes", "Nature", Sep. 28, 2000, pp. 466-467, vol. 407, No. 6803.

Dasu, V., et al., "Development of Medium for Griseofulvin Production: Part I. Screening of Medium Constituents Using the Plackett-Burman Experimental Design", "J. Microbiol. Biotechnol.", Jun. 28, 2002, pp. 355-359, vol. 12, No. 3.

Dasu, V., et al., "Development of Medium for Griseofulvin Production: Part II. Optimization of Medium Constituents Using Central Composite Design", "J. Microbiol. Biotechnol.", Jun. 28, 2002, pp. 360-366, vol. 12, No. 3.

Davis, C., et al., "*Anaerobiospirillum*, a new genus of spiral-shaped bacteria", "Int. J. Sys. Bacteriol.", Oct. 1976, pp. 498-504, vol. 26, No. 4.

Deutscher, J., et al., "How Phosphotransferase System-Related Protein Phosphorylation Regulates Carbohydrate Metabolism in Bacteria", "Microbiol. Mol. Biol. Rev.", Dec. 2006, pp. 939-1031, vol. 70, No. 4.

Donnelly, M., et al., "A novel fermentation pathway in an *Eschorichia coli* mutant producing succinic acid, acetic acid, and ethanol", "App. Biochem. Biotech.", 1998, pp. 187-198, vol. 70-72.

Hong, S., et al., "Genbank Accession No. AAU37008: PflD protein [Mannheimia succiniciproducens MBEL55E]", Oct. 2004, p. 1.

In, Y., et al., "Genbank Accession No. AAU37010: Pfl A protein [Mannheimia succiniciproducens MBEL55E]", Oct. 2004, p. 1.

Goerke, B., et al, "Carbon catabolite repression in bacteria: many ways to make the most out of nutrients", "Nature Reviews", Aug. 2008, pp. 613-624, vol. 6.

Gray, C., et al., "Regulation of metabolism in facultative bacteria: II. Effects of aerobiosis, anaerobiosis and nutrition on the formation of Krebs cycle enzymes in *Escherchia coli*", "Biochim. Biophys. Acta", Mar. 28, 1966, pp. 33-41 (Abstract), vol. 117, No. 1.

Grobben, G., et al., "Enhancement of Exopolysaccharide Production by *Lactobacillus delbrueckii* subsp. bulgaricus NCFB 2772 with a Simplified Defined Medium", "Appl. Environ. Microbiol.", Apr. 1998, pp. 1333-1337, vol. 64, No. 4.

Hong, Y., et al., "Selective extraction of succinic acid from binary mixture of succinic acid and acetic acid", "Biotechnology Letters", May 2000, pp. 871-874, vol. 22, No. 10.

Hong, S., et al., "Metabolic flux analysis for succinic acid production by recombinant *Escherichia coli* with amplified malic enzyme activity", "Biotechnol. Bioeng.", Jul. 20, 2001, pp. 89-95, vol. 74, No. 2.

Hong, S., et al., "The genome sequence of the capnophilic rumen bacterium *Mannheimia succiniciproducens* ", "Nature Biotechnology", Oct. 2004, pp. 1275-1281, vol. 22, No. 10.

Jantama, K., et al., "Combining Metabolic Engineering and Metabolic Evolution to Develop Nonrecombinant Strains of *Escherichia coli* C That Produce Succinate and Malate", "Biotechnology and Bioengineering", Oct. 30, 2007, pp. 1140-1153, vol. 99, No. 5.

Kehrenberg, C., et al., "Nucleotide sequence and organization of plasmid pMVSCS1 from Mannheimia varigena: identification of a multiresistance gene cluster", "J. Antimicrob. Chemother.", Feb. 2002, pp. 383-386, vol. 49, No. 2.

Kim, T., et al., "In silico analysis of the effects of H2 and CO2 on the metabolism of a capnophilic bacterium *Mannheimia succiniciproducens*", "Journal of Biotechnology", Jun. 17, 2009, pp. 184-189, vol. 144.

Kim, P., et al., "Effect of overexpression of actinobacillus succinogenes phosphoenolpyruvate carboxykinase on succinate production in *Escherichia coli*", "Applied and Environmental Microbiology", Feb. 2004, pp. 1238-1241, vol. 70, No. 2.

Kobayashi, K, et al., "Structure and properties of malic enzyme from Bacillus stearothermophilus", "The Journal of Biological Chemistry", Feb. 25, 1989, pp. 3200-3205, vol. 264, No. 6.

Kuhnert, P., et al., "*Basfia succiniciproducens* gen. nov., sp. nov., a new member of the family Pasteurellaceae isolated from bovine

(56) References Cited

OTHER PUBLICATIONS rumen", "International Journal of Systematic and Evolutionary Microbiology", Jul. 31, 2009, pp. 44-50, vol. 60.

Laivenieks, M., et al., "Cloning, sequencing, and overexpression of the Anaerobiospirillum succiniciproducens phosphoenolpyruvate carboxykinase (pckA) gene", "Applied and Environmental Microbiology", Jun. 1997, pp. 2273-2280, vol. 63, No. 6.

Lee, P., et al., "Succinic acid production by Anaerobiospirillum succiniciproducens: effects of the H2/CO2 supply and glucose concentration", "Enzyme Microbial Technol.", Jun. 1, 1999, pp. 549-554, vol. 24, No. 8-9.

Lee, P., et al., "Succinic acid production with reduced by-product formation in the fermentation of Anaerobiospirillum succiniciproducens using glycerol as a carbon source", "Biotechnol. Bioeng.", Jan. 5, 2001, pp. 41-48, vol. 72, No. 1.

Lee, P., et al., "Isolation and characterization of a new succinic acid-producing bacterium, Mannheimia succiniciproducens MBEL55E, from bovine rumen", "Appl. Microbiol. Biotechnol.", Feb. 8, 2002, pp. 663-668, vol. 58, No. 5.

Lee, P., et al., "Batch and continuous cultivation of Anaerobiospirillum succiniciproducens for the production of succinic acid from whey", "Applied Microbiology and Biotechnology", Jul. 2000, pp. 23-27, vol. 54, No. 1.

Lee, P., et al., "Batch and continuous cultures of Mannheimia succiniciproducens MBEL55E for the production of succinic acid from whey and corn steep liquor", "Bioprocess Biosyst Eng", Oct. 3, 2003, pp. 63-67, vol. 26.

Lee, P., et al., "Biological conversion of wood hydrolysate to succinic acid by Anaerobiospirillum succiniciproducens", "Biotechnology Letters", Jan. 2003, pp. 111-114 (Abstract), vol. 25, No. 2.

Lee, S., et al., "Genome-Based Metabolic Engineering of Mannheimia succiniciproducens for Succinic Acid Production", "Appl. Environ. Microbiol.", Mar. 2006, pp. 1939-1948, vol. 72, No. 3.

Lee, S., et al., "Metabolic Engineering of *Escherichia coli* for Enhanced Production of Succinic Acid, Based on Genome Comparison and in Silico Gene Knockout Simulation", "Appl. Environ. Microbiol.", Dec. 2005, pp. 7880-7887, vol. 71, No. 12.

Lin, H., et al., "Fed-batch culture of a metabolically engineered *Escherichia coli* strain designed for high-level succinate production and yield under aerobic conditions", "Biotechnol. Bioeng.", Jun. 20, 2005, pp. 775-779, vol. 90, No. 6.

Lin, H., et al., "Metabolic engineering of aerobic succinate production systems in *Escherichia coli* to improve process productivity and acheive the maximum theoretical succinate yield", "Metab. Eng.", Mar. 2005, pp. 116-127, vol. 7, No. 2.

Mantha, D., et al., "Optimization of medium composition by response surface methodology for the production of tartaric acid by Gluconobacter suboxydans", "Bioprocess Eng.", Oct. 1998, pp. 285-288, vol. 19, No. 3.

Kessler, D., et al, "Pyruvate-formate-lyase-deactivase and acetyl-CoA reductase activities of *Escherichia coli* reside on a polymeric protein particle encoded by adhE", "Federation of European Biochemical Societies", Apr. 1991, pp. 59-63, vol. 281, No. 1.2.

\* cited by examiner

SEQUENCE LISTING

<160> NUMBER OF SEQ ID NOS: 23

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
cagtgaagga gctccgtaac gcatccgccg                                              30

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
ctttatcgaa tctgcaggcg gtttccaaaa                                              30

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
gtactgtaaa ctgcagcttt catagttagc                                              30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gccgaaagtc aagcttgccg tcgtttagtg                                              30

<210> SEQ ID NO 5
<211> LENGTH: 10
<212> TYPE: DNA
<213> ORGANISM: Artificial Sequence
<220> FEATURE:
<223> OTHER INFORMATION: xbaI site

<400> SEQUENCE: 5
tctagaagct                                                                    10

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
gctctagacc ttctatcgcc ttcttgacg                                               29

<210> SEQ ID NO 7
<211> LENGTH: 29
<212> TYPE: DNA
<213> ORGANISM: Artificial Sequence

```
<220> FEATURE:
<223> OTHER INFORMATION: primer

<400> SEQUENCE: 7
gctctagagg ctacaaaatc acgggcgtc                                              29

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gacgtttccc gttgaatatg gc                                                     22

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
cattgaggcg tattatcagg aaac                                                   24

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
gcagtttcat ttgatgctcg atg                                                    23

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
cctcttacga tgacgcatct ttcc                                                   24

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
agcggatccc cttctatcgc cttcttgacg                                             30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
gtcctgcagg gctacaaaat cacgggcgtc                                             30
```

```
<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
gctctagata tccgcagtat cactttctgc gc                              32

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
tccgcagtcg gatccgggtt aaccgcacag                                 30

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
ggggagctcg ctaacttagc ttctaaaggc catgtttcc                       39

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
gctctagata tccgggtcaa tatcgccgca ac                              32

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
gaattcgagc tcgcccgggg atcgatcctc                                 30

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
cccgggccga caggctttga agcatgcaaa tgtcac                          36

<210> SEQ ID NO 20
<211> LENGTH: 36
<212> TYPE: DNA
<213> ORGANISM: Artificial Sequence
<220> FEATURE:
<223> OTHER INFORMATION: primer
```

```
<400> SEQUENCE: 20
cctgcaggca tgcaagcttg ggctgcaggt cgactc                    36

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
gctgccaaac aaccgaaaat accgcaataa acggc                     35

<210> SEQ ID NO 22
<211> LENGTH: 43
<212> TYPE: DNA
<213> ORGANISM: Artificial Sequence
<220> FEATURE:
<223> OTHER INFORMATION: primer

<400> SEQUENCE: 22
gcatgtaact ttactggata tagctagaaa aggcatcggg gag            43

<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
gcaacgcgag ggtcaatacc gaaggatttc gccg                      34
```

ENGINEERED MICROORGANISM PRODUCING HOMO-SUCCINIC ACID AND METHOD FOR PREPARING SUCCINIC ACID USING THE SAME

CROSS-REFERENCE TO RELATED APPLICATIONS

This application is a continuation under 35 USC 120 of U.S. patent application Ser. No. 12/359,322 filed Jan. 25, 2009, which in turn is a continuation-in-part of International Patent Application No. PCT/KR2007/003574 filed on Jul. 25, 2007 entitled "Novel Engineered Microorganism Producing Homo-Succinic Acid and Method for Preparing Succinic Acid Using the Same" in the name of Sang Yup LEE, et al., which claims priority of Korean Patent Application No. 10-2006-0071666 filed on Jul. 28, 2006. The disclosures of all of said U.S. patent application Ser. No. 12/359,322, International Patent Application No. PCT/KR2007/003574, and Korean Patent Application No. 10-2006-0071666 are hereby incorporated by reference, in their respective entireties, for all purposes.

TECHNICAL FIELD

The present invention relates to a mutant microorganism, selected from the group consisting of genus *Mannheimia*, genus *Actinobacillus* and genus *Anaerobiospirillum*, producing homo-succinic acid and a method for preparing homo-succinic acid using the same, and more particularly to a mutant microorganism, which is selected from the group consisting of genus *Mannheimia*, genus *Actinobacillus* and genus *Anaerobiospirillum*, producing succinic acid at high concentration while producing little or no other organic acids in anaerobic conditions, which is obtained by disrupting a gene encoding lactate dehydrogenase (ldhA), a gene encoding phosphotransacetylase (pta), and a gene encoding acetate kinase (ackA), without disrupting a gene encoding pyruvate formate lyase (pfl), as well as a method for preparing succinic acids using the same.

BACKGROUND ART

Succinic acid ($HOOCCH_2CH_2COOH$), a dicarboxylic acid consisting of 4 carbons, is an organic acid having high utilities, which is widely used as a precursor of medicine, food, cosmetics, and chemical products of other industries (Zeikus et al., *Appl. Microbiol. Biotechnol.*, 51:545, 1999; Song et al., *Enzyme Microbial Technol.*, 39:352, 2006). Particularly, the demand for succinic acid is expected to be dramatically increased as a main source of biodegradable macromolecules, with the latest sharp increase in petroleum prices (Willke et al., *Appl. Microbiol. Biotechnol.*, 66:131, 2004).

Succinic acid can be produced by chemical synthesis and fermentation. However, most of succinic acid for industrial use is currently produced through chemical synthesis methods using n-butane and acetylene derived from petroleum as a raw material by Chinese chemical companies, Japanese chemical companies, and big Chemical companies such as BASF, DuPont, BP chemical etc., but only a small amount of succinic acid for special use such as medicine etc. is produced by traditional microbial fermentation method. The above-mentioned chemical synthesis methods have a problem of discharging large amounts of hazardous waste, effluent, and waste gas (e.g., CO, etc.) generated during a process of producing succinic acid. Particularly, fossil fuels having high possibility of being exhausted are used as basic material, and thus there is an urgent need to develop a method for preparing succinic acids to replace the fossil fuels with alternative fuels such as renewable resources.

To overcome these problems caused by the chemical synthesis process for preparing succinic acid, studies on producing succinic acids by microbial fermentation using various renewable resources have been intensively and widely conducted by many researchers. Microorganisms, which have been used in succinic acid production, vary, but they can be generally classified into recombinant *Escherichia. coli*, ruminai bacteria (*Actinobacillus, Bacteroides, Mannheimia, Succinimonas, Succinivibrio*, etc.) and *Anaerobiospirillum* (Song et al., *Enzyme Microbial Technol.*, 39:352, 2006).

Among studies on producing succinic acids using recombinant *E. coli*, there was an attempt to increase succinic acid production by preparing a mutant AFP111 (ATCC No. 202021) obtained through a method in which a glucose transport gene (ptsG) is manipulated while genes (ldh and pfl), which are involved in producing lactic acid and formic acid in *E. coli*, are eliminated, by the University of Chicago research team (U.S. Pat. No. 5,770,435).

The present inventors have amplified a malic enzyme gene (sfcA) involved in succinic acid production, in recombinant *E. coli*, NZN111 strain, from which ldh and pfl genes are eliminated, to suppress pyruvic acid accumulated in the fermentation process of the NZN111 strain, thus increasing succinic acid production (Hong et al., *Biotechnol. Bioeng.*, 74:89, 2001). Also, a Georgia University-led team of researchers has constructed an AFP111/pTrc99A-pyc strain by expressing a pyruvate carboxylase gene (pyc) in the AFP 111 strain, and then used this strain in producing succinic acid (Vemuri et al., *J. Ind. Microbiol. Biotechnol.*, 28:325, 2001). Recently, in order to induce the production of succinic acid in anaerobic conditions, a Rice University-led team of researchers reported that they have constructed recombinant *E. coli* strains by manipulating genes involved in pathways of Glycolysis, TCA cycle, and Glyoxylate (Lin et al., *Eng.*, 7:116, 2005; Lin et al., *Biotechnol. Bioeng.*, 90:775, 2005).

*Actinobacillus* strain and *Mannheimia* strain, which are a kind of rumen bacteria, and *Anaerobiospirillum* strain, are known to be excellent in producing succinic acid, so that studies on the strains have been actively conducted. Michigan Biotechnology Institute (MBI)-led team of researchers in America discovered *Actinobacillus succinogenes* 130Z strain (ATCC No. 55618) to develop a method for producing succinic acid, and constructed various mutant strains of *Actinobacillus succinogenes*, using traditional chemical mutagenesis to use in developing a process for producing and purifying succinic acid (U.S. Pat. No. 5,521,075; U.S. Pat. No. 5,168,055; U.S. Pat. No. 5,143,834).

However, succinic acid production process using microbial fermentation, developed until now, has a very low productivity of less than 2 g/L/h, and especially it incurs a huge cost to separate and purify succinic acid because succinic acid is produced together with large amounts of various organic acids and ethanol as byproducts to some degree during fermentation. Although the above-mentioned results showed an effect of decreasing lactic acid, formic acid, acetic acid, and ethanol as byproducts in some recombinant strains, they did not show complete elimination of them. In addition, in another recombinant mutant strains, there were some cases where the growth rates of them have become so low that overall succinic acid productivity was not increased. Therefore, there is an urgent demand to develop a novel succinic acid-producing strain, which has a high productivity of succinic acid and prevents the production of byproducts (Hong et al., *Biotechnol. Lett.,* 22:871, 2000).

To develop a novel succinic acid-producing strain to satisfy the above demands, isolation of a strain having excellent succinic acid productivity, completion of genome sequence thereof, an understanding of metabolic characteristic thereof, and establishing a genetic manipulation technique required for the construction of a recombinant strain should be preceded. Up to now, in the case of bacteria having high succinic acid productivity, the full genome sequence of strain *M succiniciproducens* MBEL 55E (KCTC 0769BP) was completed, but those of bacteria such as *Actinobacillus, Anaerobiospirillum* etc. have not been reported yet. Although an attempt to try to produce succinic acids by amplifying phosphoenolpyruvate carboxykinase gene (pckA) of *A. succinogenes* and *A. succiniciproducens* in *E. coli*, has been reported (Kim et al., *Appl. Environ. Microbiol.,* 70:1238, 2004; Laivenieks et al., *Appl. Environ. Microbiol.,* 63:2273, 1997), there has been no attempt to try to develop a recombinant succinic acid production strain based on genome sequence.

The present inventors have reported that they isolated *M. succiniciproducens* MBEL 55E (KCTC0769BP) producing succinic acid with high efficiency from Korean native cattle, and completed genome sequence and characterized metabolic properties of the strain (Hong et al., *Nature Biotechnol.,* 22: 1275, 2004). Also, the present inventors have constructed a bacterial mutant, *M. succiniciproducens* LPK (KCTC10558BP) by disrupting a gene encoding lactate dehydrogenase (ldhA) and a gene encoding pyruvate formate-lyase (pfl) in *M. succiniciproducens* MBEL 55E (KCTC 0769BP) which is a kind of rumen bacteria in order to inhibit the production of lactic acids and formic acids. In addition to that, the present inventions have constructed a mutant *M. succiniciproducens* LPK7 (KCTC1062BP) by disrupting a phosphotransacetylase gene (pta) and an acetate kinase gene (ackA) in the mutant strain, *M. succiniciproducens* LPK in order to inhibit the production of acetic acid, to culture the bacterial mutants in anaerobic conditions (WO 05/052135 A 1; Lee et al., *Appl. Environ. Microbiol.* 72:1939, 2006), thus increasing succinic acid. However, in case of such mutant strains, although the production of byproducts, formic acid and acetic acid could be suppressed to some extent, a large amount of pyruvic acids were accumulated as a byproduct during fermentation, most of all, the growth rate of the strain has become so low compared with a wild strain that an excellent succinic acid productivity could not be achieved.

Meanwhile, it was reported that a pyruvate formate-lyase gene (pfl) participates in conversion of pyruvic acid into acetyl Coenzyme A (acetyl-CoA), thus affecting cell growth and redistribution of pyruvic acid (Wolfe, *Microbial. Mol. Biot. Rev.,* 69:12, 2005).

Accordingly, the present inventors have made extensive efforts to construct a mutant microorganism capable of producing homo-succinic acids at a high yield by minimizing a decrease in microbial growth rate and completely inhibiting the formation of various byproducts including pyruvic acids and to develop a fermentation method thereof, and as a result, they have constructed a bacterial mutant *M. succiniciproducens* PALK (KCTC10973BP) by disrupting a lactate dehydrogenase gene (ldhA), a phosphotransacetylase gene (pta) and an acetate kinase gene (ackA) without disrupting a pyruvate formate-lyase gene (pfl) in *M. succiniciproducens* MBEL55E (KCTC 0769BP) which is a kind of rumen bacteria, and then fermentated the mutant strain in anaerobic conditions using glucose and glycerol as carbon sources, and confirmed that the mutant strain can produce nearly homo-succinic acid at a high yield, thereby completing the present invention.

SUMMARY OF THE INVENTION

Therefore, it is an object of the present invention to provide a mutant microorganism that has high growth rate and succinic acid productivity and produces only succinic acid at a high yield while producing little or no other organic acids during the period of anaerobic fermentation.

Another object of the present invention is to provide a method for producing homo-succinic acid without the accumulation of other byproducts, by culturing the mutant microorganism using glucose and glycerol as carbon sources in anaerobic conditions.

To achieve the above objects, the present invention provides a mutant microorganism lacking a lactate dehydrogenase gene (ldhA), a phosphotransacetylase gene (pta), and an acetate kinase gene (ackA) while comprising a pyruvate formate-lyase gene (pfl), which has the property of producing only succinic acid at a high concentration while producing little or no other organic acids in anaerobic conditions, wherein the microorganism is selected from the group consisting of genus *Mannheimia*, genus *Actinobacillus* and genus *Anaerobiospirillum*.

Also, the present invention provides a mutant microorganism *Mannheimia succiniciproducens* PALK (KCTC10973BP) lacking a lactate dehydrogenase gene (ldhA), a phosphotransacetylase gene (pta), and an acetate kinase gene (ackA) while comprising a pyruvate formate-lyase gene (pfl) in *M. succiniciproducens*, which has the property of producing succinic acid at a high concentration while producing little or no other organic acids in anaerobic conditions.

Additionally, the present invention provides a method for producing a mutant microorganism, the method comprising the steps of: (a) obtaining a mutant microorganism lacking the gene encoding lactate dehydrogenase (ldhA) by disrupting a gene encoding lactate dehydrogenase (ldhA) from the genome of succinic acid producing microorganism which is selected from the group consisting of genus *Mannheimia*, genus *Actinobacillus* and genus *Anaerobiospirillum*, using homologous recombination; and (b) obtaining a mutant microorganism lacking a gene encoding lactate dehydrogenase (ldhA), a gene encoding phosphotransacetylase (pta), and a gene encoding acetate kinase (ackA) by disrupting a gene encoding phosphotransacetylase (pta) and a gene encoding acetate kinase (ackA), from the genome of the mutant microorganism lacking the gene encoding lactate dehydrogenase (ldhA), by homologous recombination.

Further, the present invention provides a method for producing succinic acid, the method comprising the steps of: culturing the mutant microorganisms in anaerobic conditions; and recovering succinic acid from the culture broth.

Another features and embodiments of the present invention will be more clarified from the following detailed descriptions and the appended claims.

DETAILED DESCRIPTION OF THE INVENTION, AND PREFERRED EMBODIMENTS

Figure 1:
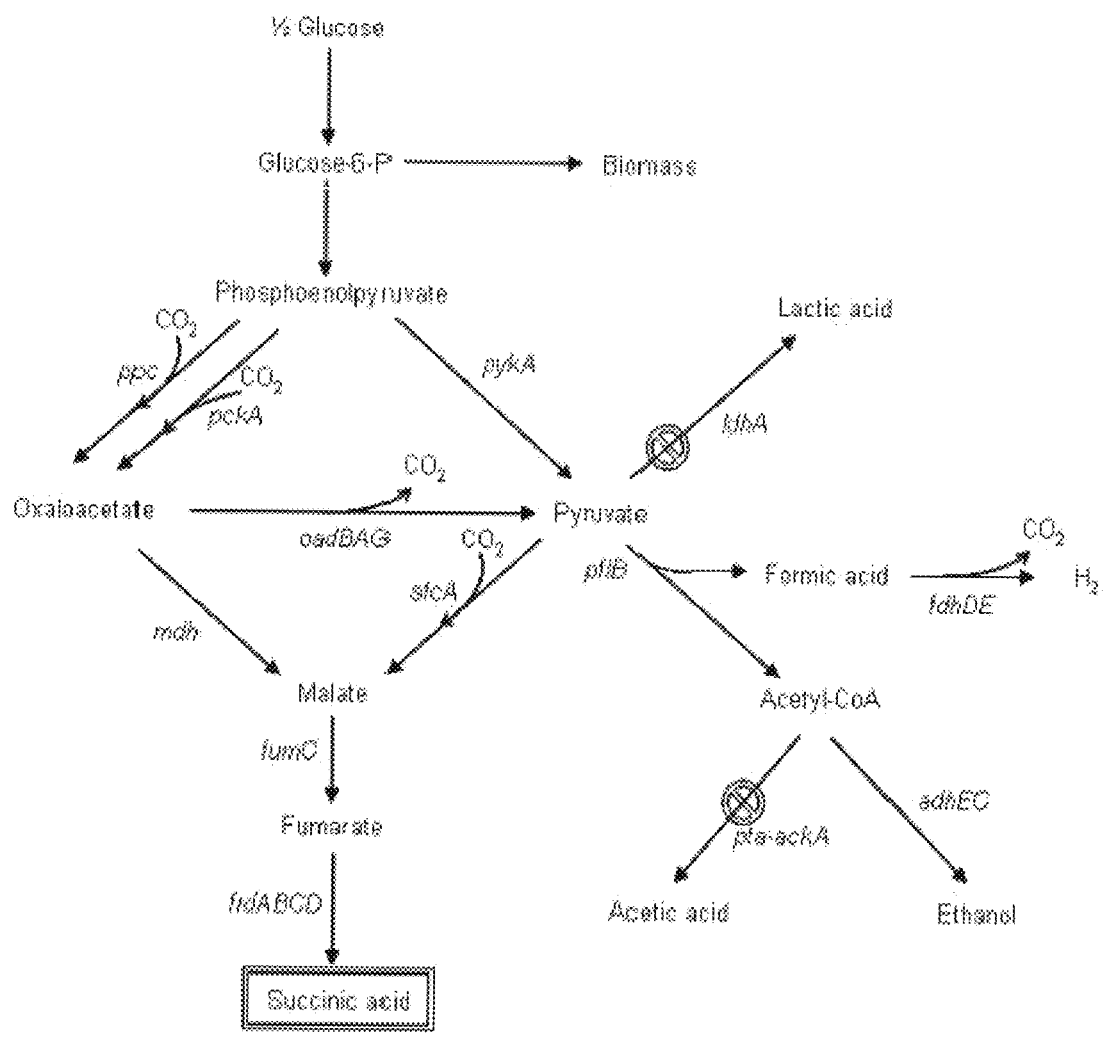
FIG. 1 is a schematic diagram showing the succinic acid production pathway in the mutant microorganism according to the present invention.

In one aspect, the present invention relates to a mutant microorganism lacking a lactate dehydrogenase gene (ldhA), a phosphotransacetylase gene (pta), and an acetate kinase gene (ackA) while comprising a pyruvate formate-lyase gene (pfl), which has the property of producing only succinic acid at a high concentration while producing little or no other organic acids in anaerobic conditions, wherein the microorganism is selected from the group consisting of genus *Mannheimia*, genus *Actinobacillus* and genus *Anaerobiospirillum*.

In the present invention, the succlmc acid-producing microorganism refers to a microorganism capable of producing an excessive large amount of succinic acid compared to the production of ethanol or other organic acids, which can be used for industrial use in succinic acid production by fermentation.

Typical succinic acid-producing microorganisms include rumen bacteria and other kind of bacteria producing succinic acids such as *Anaerobiospirillum succiniciproducens*. From partial genetic information (16s rRNA), enzyme analysis, and fermentation results of *Actinobacillus succinogenes* and *M. succiniciproducens* and which are a kind of rumen bacteria, and *Anaerobiospirillum succiniciproducens*, and various bacteria which are known to produce succinic acid until now, it was found that main biosynthesis pathway for succinic acid production from a carbon source in succinic acid-producing microorganisms is almost identical with biosynthesis pathway for succinic acid production in *Mannheimia* sp. which is a kind of rumen bacteria (Table 1; Van der Werf et al., *Arch Microbiol.*, 167:332, 1997; Laivenieks et al., *Appl. Environ. Microbiol.*, 63:2273, 1997; Samuelov et al., *App. Environ. Microbiol.*, 65:2260, 1999; Kim et al., *Appl. Environ. Microbiol.*, 70:1238, 2004). Especially all rumen bacteria and *A. succiniciproducens*, which are involved in the production of succinic acid, convert phosphoenolpyruvate and pyruvate, C3 compounds into oxaloacetate and malate, C4 compounds using $CO_2$-fixing enzyme upon succinic acid production, thus producing succinic acid. In addition, rumen bacteria and *A. succinicipro-* *ducens* produce acetic acid, formic acid, and lactic acid as fermentation byproducts in anaerobic conditions, thus suggesting that all rumen bacteria, including the *Mannheimia* sp., and *A. succiniciproducens* have the same pathway for succinic acid biosynthesis.

TABLE 1

Succinic acid producing microorganisms

| Strain | References |
| --- | --- |
| *Cytophaga succinicans* | Anderson et al., *J Bacteriol.*, 81: 130, 1961 |
| *Fibrobacter succinogens* | Wood et al., *J Cereal. Sei.*, 19: 65, 1994 |
| *Ruminococcus flavefaciens* | Iannotti et al., *Appl. Environ. Microbiol.*, 43: 136, 1973 |
| *Succinimonas amylolytica* | Bryant, *Bacteriol. Rev.*, 23: 125, 1959 |
| *Succinivibrio dextrinisolvens* | Bryant, *Bacteriol. Rev.*, 23: 125, 1959 |
| *Actinobacillus succinogenes* | Glutter et al., !nt. *J Syst. Bacteriol.*, 49: 207, 1999 |
| *Mannheimia succiniciproducens* | Hong et al., *Nature Biotechnol.*, 22: 1275, 2004 |

In the present invention, a succinic acid-producing mutant microorganism with a high growth rate, which is capable of producing succinic acid at a high concentration while producing little or no other organic acids, was constructed by manipulating the genome of a succinic acid-producing microorganism. In other words, a lactate dehydrogenase gene (ldhA), a phosphotransacetylase gene (pta), and an acetate kinase gene (ackA) were disrupted in the genome DNA of *M. succiniciproducens* MBEL55E (KCTC0769BP), thereby constructing a bacterial mutant *M. succiniciproducens* PALK (KCTC 10973BP) which shows a high growth rate and produces succinic acid at a high concentration while producing little or no other organic acids.

In the present invention, for the disruption of each gene, a method of substituting the genes by homologous recombination to inactivate was used, but any method can be used without limitations as long as it is genetic manipulation method where the corresponding gene can be modified or eliminated, such that an enzyme encoded by the corresponding gene is not generated.

In the present invention, the said succinic acid-producing microorganisms are *Anaerobiospirillum* sp. bacteria or rumen bacteria which are selected from the group consisting of *Mannheimia* sp. and *Actinobacillus* sp.

In the present invention, the mutant microorganism is preferably a homogeneous fermentation strain producing only succinic acid while forming little or no other organic acids as byproducts, the each amounts—of other organic acids produced is preferably less than 1 wt % based on the amount of succinic acid produced, and the other organic acids are preferably any one or more organic acids selected from the group consisting of lactic acid, acetic acid, formic acid, and pyruvic acid.

In another aspect, the present invention relates to a rumen bacterial mutant *M. succiniciproducens* PALK (KCTC 10973BP), lacking a lactate dehydrogenase gene (ldhA), a phosphotransacetylase gene (pta), and an acetate kinase gene (ackA) in *M. succiniciproducens* while a pyruvate formate-lyase gene (pfl) is maintained in *M. succiniciproducens*, which has the property of producing succinic acid at a high concentration while producing little or no other organic acids in anaerobic conditions.

The bacterial mutant *M. succiniciproducens* LPK7 (KCTC10626BP), which was constructed by disrupting a gene encoding lactate dehydrogenase (ldhA), a gene encoding pyruvate formate-lyase (pfl), a gene encoding phosphotransacetylase (pta), and a gene encoding acetate kinase (ackA) in the genome of *Mannheimia* sp., was used in order to compare the succinic acid productivity and growth rate of *M. succiniciproducens* PALK (KCTC10973BP) according to the present invention with those of traditional bacterial mutants. Herein, the bacterial mutant *M. succiniciproducens* LPK7 (KCTC10626BP) has an additional disruption of a gene encoding pyruvate formate-lyase (pfl) in the mutant strain *M. succiniciproducens* PALK (KCTC10973BP) according to the present invention (WO2005/052135; Lee et al., *Appl. Environ. Microbiol.* 72: 1939, 2006).

*M. succiniciproducens* PALK (KCTC10973BP) according to the present invention has a high succinic acid productivity and produces little or no byproducts such as lactic acid, acetic acid, formic acid, and pyruvic acid, thus showing excellent properties compared to wild-type *M. succiniciproducens* MBEL55E (KCTC0769BP) for succinic acid production and previously constructed bacterial mutant *M. succiniciproducens* LPK7 (KCTC10626BP), and can produce succinic acid at a high yields due to a high growth rate thereof, high succmlc acid productivity and homo-succinic acid production by preventing pyruvlc acid accumulation, compared to previously constructed bacterial mutant *M. succiniciproducens* LPK7 (KCTC10626BP).

In still another aspect, the present invention relates to a method for constructing a mutant microorganism, the method comprising the steps of: (a) obtaining a mutant microorganism lacking a gene encoding lactate dehydrogenase (ldhA) by disrupting a gene encoding lactate dehydrogenase (ldhA) in genome of succinic acid producing microorganism which is selected from the group consisting of genus *Mannheimia*, genus *Actinobacillus* and genus *Anaerobiospirillum*, using homologous recombination; and (b) obtaining a mutant microorganism lacking a gene encoding lactate dehydrogenase (ldhA), a gene encoding phosphotransacetylase (pta), and a gene encoding acetate kinase (ackA) by disrupting a gene encoding phosphotransacetylase (pta) and a gene encoding acetate kinase (ackA) in genome of the mutant microorganism lacking a gene encoding lactate dehydrogenase (ldhA) using homologous recombination.

In the present invention, the homologous recombination of the step (a) is preferably performed using a genetic exchange vector containing a disrupted ldhA, and the homologous recombination of the step (b) is preferably performed using a genetic exchange vector containing a disrupted pta-ackA.

In the present invention, the genetic exchange vector containing a disrupted ldhA is preferably pMLKO-sacB, and the genetic exchange vector containing a disrupted pta-ackA is preferably pMPKO-sacB.

The present invention also provides a method for producing succmlc acid, the method comprising the steps of: culturing the above-mentioned mutant microorganism in anaerobic conditions; and recovering succinic acid from the culture broth.

In the present invention, for the culture, glucose or glycerol is preferably used as a carbon source, and the each amount of other organic acids produced as byproducts is preferably less than 1 wt % based on the amount of succinic acid produced.

In yet another aspect, the present invention relates to a method for preparing succinic acid, the method comprising the steps of: culturing the mutant microorganism in anaerobic conditions; and recovering succinic acid from the culture broth.

The culture of the succinic acid producing mutant microorganism according to the present invention and recovery process of succinic acid can be performed by the culture methods known in the conventional fermentation process and methods for separating and purifying succinic acid.

In the present invention, for the culture, glucose or glycerol is preferably used as a carbon source, and the each amounts of other organic acids produced as byproducts is preferably less than 1 wt % based on the amount of succinic acid produced.

EXAMPLES

The present invention will hereinafter be described in further details by examples. It will however be obvious to a person skilled in the art that these examples are given for illustrative purpose only, and the present invention is not limited to or by the examples.

Particularly, the following examples illustrate only *Mannheimia* sp. which is a succinic acid-producing microorganism as a host cell in order to delete the genes according to the present invention. However, it is obvious to a person skilled in the art that a mutant microorganism producing homo-succinic acid can be obtained even when other kinds of succinic acid producing microorganisms are used.

Example 1

Construction of ldhA Disruption Vector (pMLKO-sacB)

In order to disrupt a lactate dehydrogenase gene (ldhA) in the genome of a succinic acid-producing microorganism by homologous recombination, a gene exchange vector was constructed in the following manner. First, the genomic DNA of *M. succiniciproducens* MBEL55E (KCTC 0769BP), as a template, was subjected to PCR using primers set forth in SEQ ID NO: 1 and SEQ ID NO: 2 below, and then, the obtained PCR fragment containing ldhA-homologous region 1 (L1) was cut with SacI and PstI and introduced into pUC18 vector (New England Biolabs, Inc., USA), thereby constructing pUC18-L1.

```
SEQ ID NO: 1:
5'-CAGTGAAGGAGCTCCGTAACGCA TCCGCCG

SEQ ID NO: 2:
5'-CTTTATCGAATCTGCAGGCGGTTTCCAAAA
```

In addition, the genomic DNA of *M. succiniciproducens* MBEL55E (KCTC 0769BP), as a template, was subjected to PCR using primers set forth in SEQ ID NO: 3 and SEQ ID NO: 4 below, and then, the obtained PCR fragment containing ldhA-homologous region 2 (L2) was cut with PstI and HindIII and introduced into the pUC18-L1, thereby constructing pUC18-L1-L2.

```
SEQ ID NO: 3:
5'-GTACTGTAAACTGCAGCTTTCA TAGTTAGC

SEQ ID NO: 4:
5'-GCCGAAAGTCAAGCTTGCCGTCGTTT AGTG
```

In order to insert kanamycin-resistant gene as a selection marker in the pUC18-L1-L2, pUC4K vector (Pharmacia, Germany) was cut with PstI, and the resulting kanamycin-resistant gene was fused with pUC18-L1-L2 cut with PstI, thereby constructing pUC18-L1-KmR-L2. A linker set forth in SEQ ID NO: 5 was inserted into the pUC18-L1-KmR-L2 cut with SacI, thereby making a new XbaI cutting site.

```
SEQ ID NO: 5:
5'-TCTAGAAGCT
```

Figure 2:
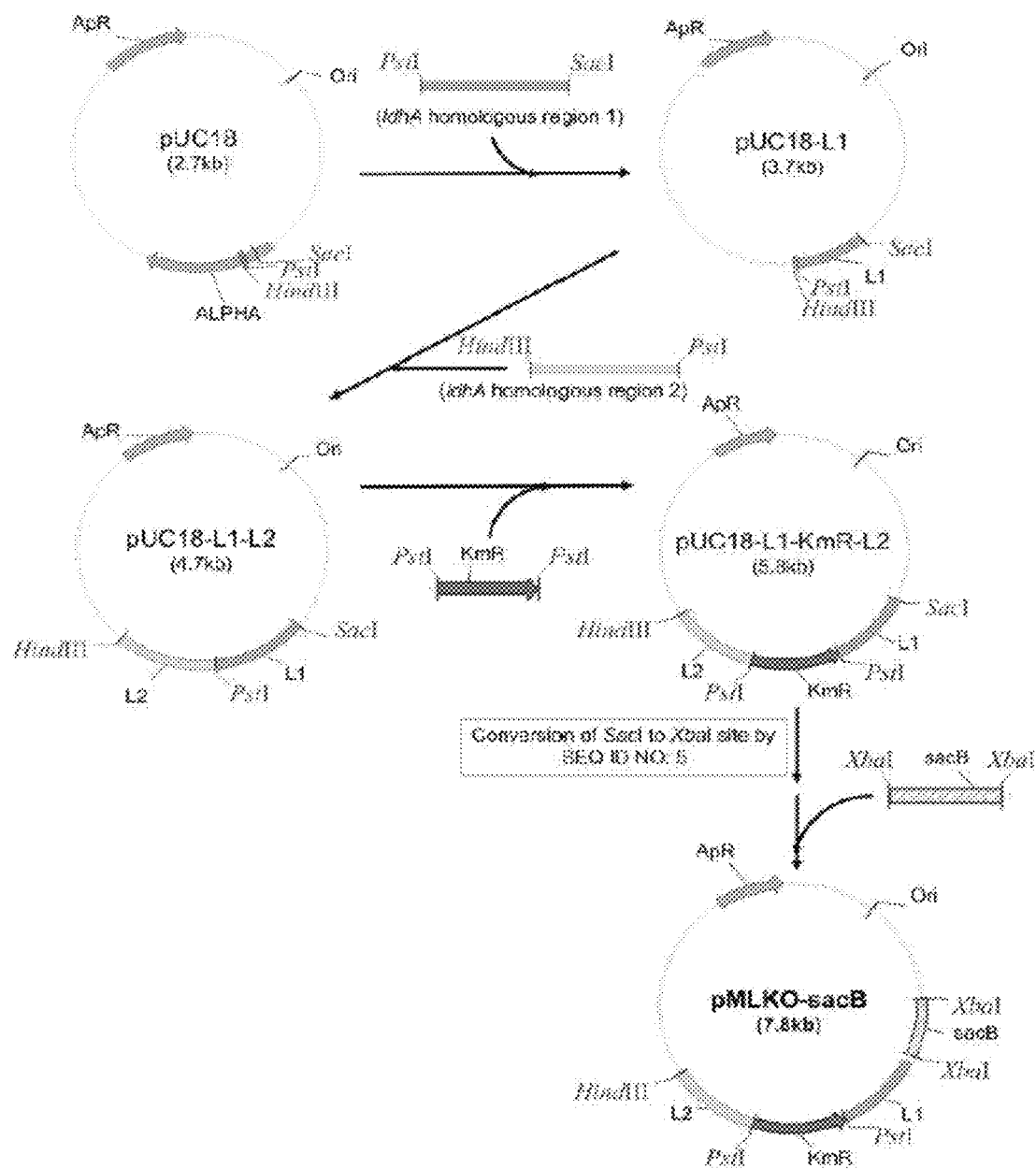
FIG. 2 shows a process of constructing a replacement vector for disrupting ldhA (pMLKO-sacB) by homologous recombination.

In order to insert sacB gene in the pUC18-L1-KmR-L2 into which the XbaI cutting site has been inserted, PCR on pKmobsacB (Schafer et al., *Gene*, 145:69, 1994) as a template was performed using primers set forth in SEQ ID NO: 6 and 7. Then the resulting PCR fragment containing sacB gene was cut with XbaI, and inserted into the new XbaI restriction enzyme site of pUC18-L1-KmR-L2 into which the above XbaI cutting site has been inserted, thereby constructing pMLKO-sacB, an exchange vector for disrupting ldhA gene (FIG. 2).

```
SEQ ID NO: 6:
5'-GCTCTAGACCTTCTATCGCCTTCTTGACG

SEQ ID NO: 7:
5'-GCTCTAGAGGCTACAAAATCACGGGCGTC
```

Example 2

Construction of *M. Succinici Producens* LK Strain

Figure 3:
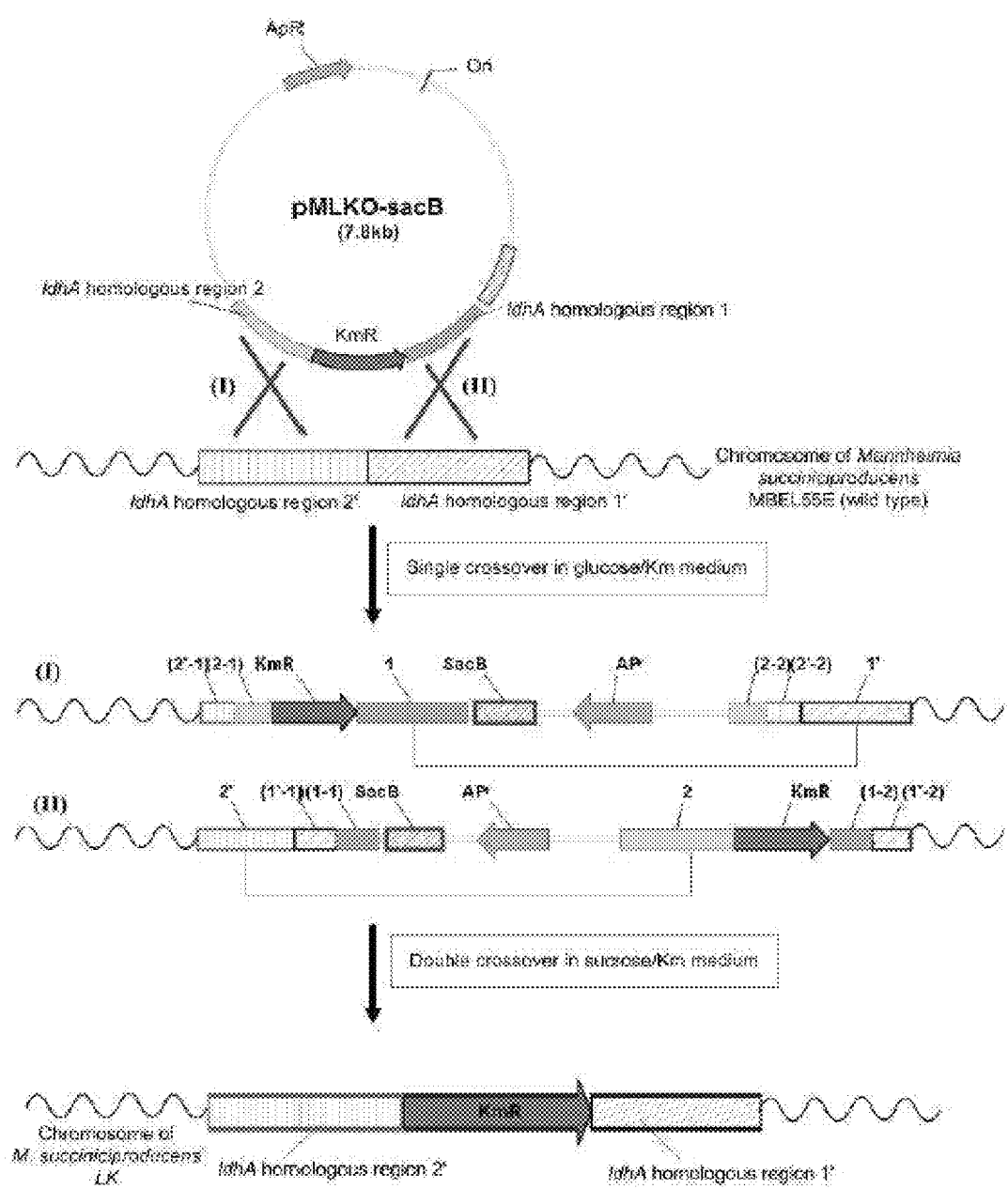
FIG. 3 shows a process of constructing a bacterial mutant (*M. succinicproducens* LK) by disrupting ldhA gene in *Mannheimia succiniciproducens* MBEL55E by homologous recombination.

A mutant strain was constructed by disrupting ldhA gene in the genome of *M. succiniciproducens* MBEL55E (KCTC0769BP) using pMLKO-sacB constructed in Example 1 as a genetic exchange vector for disrupting ldhA gene (FIG. 3).

In other words, *M. succiniciproducens* MBEL55E (KCTC0769BP) was plated on LB-glucose agar medium containing 10 g/L of glucose, and cultured at 37° C. for 36 hours. The colony formed was inoculated in 10 ml of LB-glucose liquid medium, and cultured for 12 hours. 1% of the culture broth, which had been sufficiently grown, was inoculated in 100 ml of LB-glucose liquid medium, and cultured in a shaking incubator at 200 rpm and 37° C.

When the culture broth reached an $OD_{600}$ of about 0.3-0.4 after 4-5 hours, it was centrifuged at 4° C. and 4,500 rpm for 20 minutes to collect cells. Then, the cells were resuspended in 200 ml of 10% glycerol solution at 4° C. The suspension was centrifuged at 4° C. and 5,500 rpm for 20 minutes, and the cells were collected. After resuspending and collecting in one-half of the above glycerol solution twice in the same manner as the above-described processes, the cells were suspended in glycerol at a volume ratio of 1:1, to obtain cell concentrate.

The cell concentrate thus obtained was mixed with the genetic exchange vector pMLKO-sacB constructed in Example 1, and then pMLKO-sacB was introduced into the cultured *M. succiniciproducens* MBEL55E (KCTC0769BP) by electroporation under conditions of 1.8 kV, 25 μF and 200 ohms 1 ml of LB-glucose liquid medium was added to the pMLKO-sacB-introduced strain, and precultured in a shaking incubator at 37° C. and 200 rpm for one hour. The culture broth was plated on LB-glucose solid medium containing an antibiotic kanamycin (final concentration of 25 μg/ml) and cultured at 37° C. for 48 hours or more. In order to select a colony where only double crossover occurred, the colonies formed were streaked on LB-sucrose solid medium containing kanamycin (25 μg/ml) and 100 g/L sucrose. After 24 hours, the formed colonies were streaked again on the same medium.

The colonies (mutant) formed on the medium were cultured in LB-glucose liquid medium containing an antibiotic, and genomic DNA was isolated from the cultured strain by the method described in Rochelle et al. (Rochelle et al., *FEMS Microbiol. Lett.*, 100:59, 1992). PCR was performed using the isolated mutant genomic DNA as a template, and the PCR product was electrophoresed to confirm the disruption of ldhA gene in the genomic DNA.

In order to confirm the disruption of the ldhA gene, PCRs were performed twice in the following manners. First, the mutant genomic DNA as a template was subjected to PCR using primers set forth in SEQ ID NO: 8 and SEQ ID NO: 9.

```
SEQ ID NO: 8:
5'-GACGTTTCCCGTTGAATATGGC (KM I)

SEQ ID NO: 9:
5'-CATTGAGGCGTATTATCAGGAAAC (LU I)
```

Then, the mutant genomic DNA as a template was subjected to PCR using primers set forth in SEQ ID NO: 10 and SEQ ID NO: 11.

```
SEQ ID NO: 10:
5'-GCAGTTTCATTTGATGCTCGATG (KM2)

SEQ ID NO: 11:
5'-CCTCTTACGATGACGCATCTTTCC (LD2)
```

The PCR fragments obtained in the two PCRs were subjected to gel electrophoresis to confirm the disruption of ldhA by their size. The PCR fragments of the genomic DNA having disrupted ldhA were confirmed by the fact that the product resulted from the PCR using the primers of SEQ ID NO: 8 (KM1) and SEQ ID NO: 9 (LU1) has a size of 1.5 kb, and at the same time the product resulted from the PCR using the primers of SEQ ID NO: 10 (KM2) and SEQ ID NO: 11 (LU2) has a size of 1.7 kb. The position of each primer is shown in FIG. 3.

The mutant strain *M. succiniciproducens* LK was constructed by disrupting ldhA gene in the genome of *M. succiniciproducens* MBEL55E according to the above method.

Example 3

Figure 4:
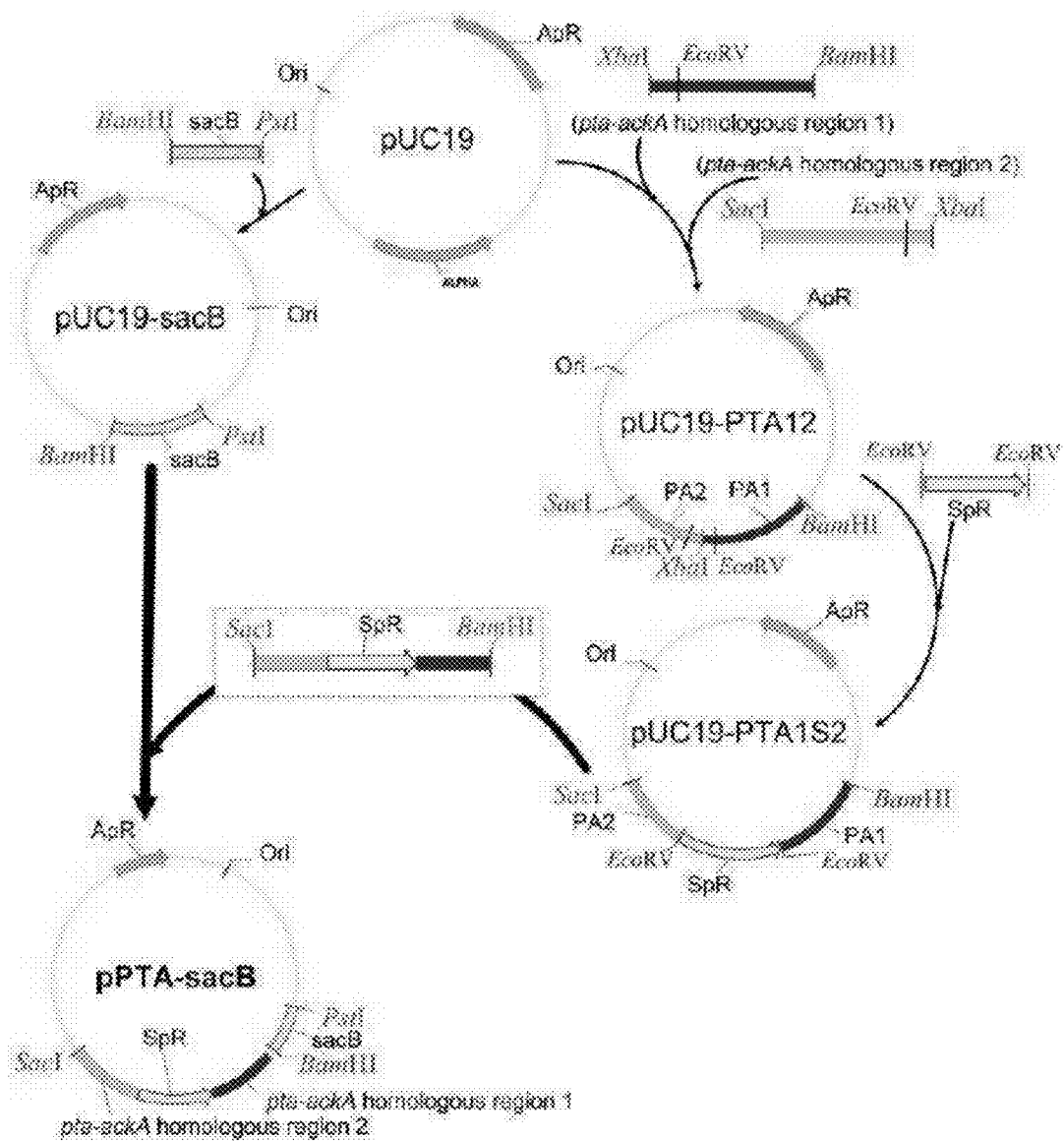
FIG. 4 shows a process of constructing a replacement vector for disrupting pta and ackA (pPTA-sacB) by homologous recombination.

Construction of Gene Exchange Vector (pPTA-sacB) for the Disruption of pta and ackA In order to disrupt pta and ackA in the genome of *M. succinicproducens* LK strain by homologous recombination, a genetic exchange vector was constructed in the following manner. A vector pKmobsacB containing a sacB gene, as a template, was subjected to PCR using primers set forth in SEQ ID NO: 12 and SEQ ID NO: 13. The resulting sacB product was cut with PstI and BamHI and inserted into pUC19 (Stratagene Cloning Systems. USA), thereby constructing pUC19-sacB (FIG. 4).

```
SEQ ID NO: 12:
5'-AGCGGATCCCCTTCTATCGCCTTCTTGACG

SEQ ID NO: 13:
5'-GTCCTGCAGGGCTACAAAA TCACGGGCGTC
```

Meanwhile, the genomic DNA of *M. succiniciproducens* LK as a template was subjected to PCR using primers set forth in SEQ ID NO: 14 and SEQ ID NO: 15, and the resulting PCR fragment containing pta-ackA homologous region 1 was cut with XbaI and BamH I. In addition, the genomic DNA of *M. succiniciproducens* LK as a template was subjected to PCR using primers set forth in SEQ ID NO: 16 and SEQ ID NO: 17, and the resulting PCR fragment containing pta-ackA homologous region 2 was cut with XbaI and SacI. Then, these fragments were inserted into BamHI and SacI site of pUC19, thereby constructing pUC19-PTA12.

```
SEQ ID NO: 14:
5'-GCTCTAGATATCCGCAGTATCACTTTCTGCGC

SEQ ID NO: 15:
5'-TCCGCAGTCGGATCCGGGTTAACCGCACAG

SEQ ID NO: 16:
5'-GGGGAGCTCGCTAACTTAGCTTCTAAAGGCCA TGTTTCC

SEQ ID NO: 17:
5'-GCTCTAGATATCCGGGTCAATATCGCCGCAAC
```

In order to insert a spectinomycin-resistant gene (GenBank X02588; SpR) as a selective marker in pUC19-PTA12, plasmid pIC156 (Steinmetz et al., *Gene*, 142:79, 1994) containing a spectinomycin-resistant gene (GenBank X02588), as a template, was subjected to PCR using primers set forth in SEQ ID NO: 18 and SEQ ID NO: 19, and the resulting PCR fragment containing SpR gene was cut with EcoRV and introduced into the pUC19-PTA12, thereby constructing pUC19-PTA1S2 having the spectinomycin-resistant gene. The constructed pUC19-PTA1S2 was cut with SacI and BamHI and introduced into the above constructed pUC19-SacB, thereby constructing an exchange vector (pPTA-sacB) for the disruption of pta and ackA (FIG. 4).

```
SEQ ID NO: 18:
5'-GAATTCGAGCTCGCCCGGGGATCGATCCTC

SEQ ID NO: 19:
5'-CCCGGGCCGACAGGCTTTGAAGCATGCAAATGTCAC
```

Example 4

Construction of *M. succiniciproducens* PALK Strain

A mutant strain was constructed by disrupting pta and ackA gene in the genome of *M. succiniciproducens* LK using pPTA-sacB, an exchange vector for the disruption of phosphotransacetylase gene (pta) and acetate kinase gene (ackA) constructed in Example 3 (FIG. 4).

In other words, *M. succiniciproducens* LK constructed in Example 2 was plated on LB-glucose agar medium containing 10 g/L of glucose, and cultured at 37° C. for 36 hours. The colony formed was inoculated in 10 ml of LB-glucose liquid medium, and cultured for 12 hours. 1% of the culture broth, which had been sufficiently grown, was inoculated in 100 ml of LB-glucose liquid medium, and cultured in a shaking incubator at 200 rpm and 37° C.

Cell concentrate was collected from the resulting culture broth in the same manner as described in Example 2. The collected cell concentrate was mixed with the genetic exchange vector pPTA-sacB constructed in Examples 3, and then pPTA-sacB was introduced into the *M succiniciproducens* LK by electroporation under conditions of 2.5 kV, 50 μF and 200 ohms 800 ml of LB-glucose liquid medium was added to the pPTA-sacB-introduced strain, and precultured in a thermostat at 37° C. for one and a half hour. In order to induce a double crossover, the culture broth was plated on TSB-sucrose solid medium (Tryptic Soy Broth (Becton, Dickinson and Company) solid medium containing 100 g/L of sucrose) containing an antibiotic spectinomycin (final concentration of 50 μg/ml) and cultured at 37° C. for 48 hours or more. In order to screening a colony where only double crossover occurred, the colonies formed were streaked on TSB-sucrose medium containing 50 μg/ml spectinomycin and TSB agar medium containing 50 μg/ml ampicillin, respectively, and cultured at 37° C. for 12 hours. Then, the colonies, which were formed on the TSB-sucrose medium containing 50 μg/ml spectinomycin but not formed on the TSB medium containing 50 μg/ml ampicillin, were selected and streaked again on the TSB-sucrose medium containing 50 μg/ml spectinomycin. The colonies formed herein were screened again using the spectinomycin-containing medium and the ampicillin-containing medium, and then the colonies which showed required results were selected ultimately. The isolated mutant genomic DNA as a template was amplified by PCR and the PCR product was electrophoresed to confirm the disruption of pta-ackA.

To confirm the disruption of pta-ackA, PCRs were performed twice m the following manner. First, the mutant genomic DNA as a template was subjected to PCR using primers set forth in SEQ ID NO: 20 and SEQ ID NO: 21. Then, the mutant genomic DNA as a template was subjected to PCR using primers set forth in SEQ ID NO: 22 and SEQ ID NO: 23.

```
SEQ ID NO: 20:
5'-CCTGCAGGCATGCAAGCTTGGGCTGCAGGTCGACTC (SP1)

SEQ ID NO: 21:
5'-GCTGCCAAACAACCGAAAATACCGCAATAAACGGC (PAU1)

SEQ ID NO: 22:
5'-GCATGTAACTTTACTGGATATAGCTAGAAAAGGCATCGGGGAG (SP2)

SEQ ID NO: 23:
5'-GCAACGCGAGGGTCAATACCGAAGGATTTCGCCG (PAD2)
```

Figure 5:
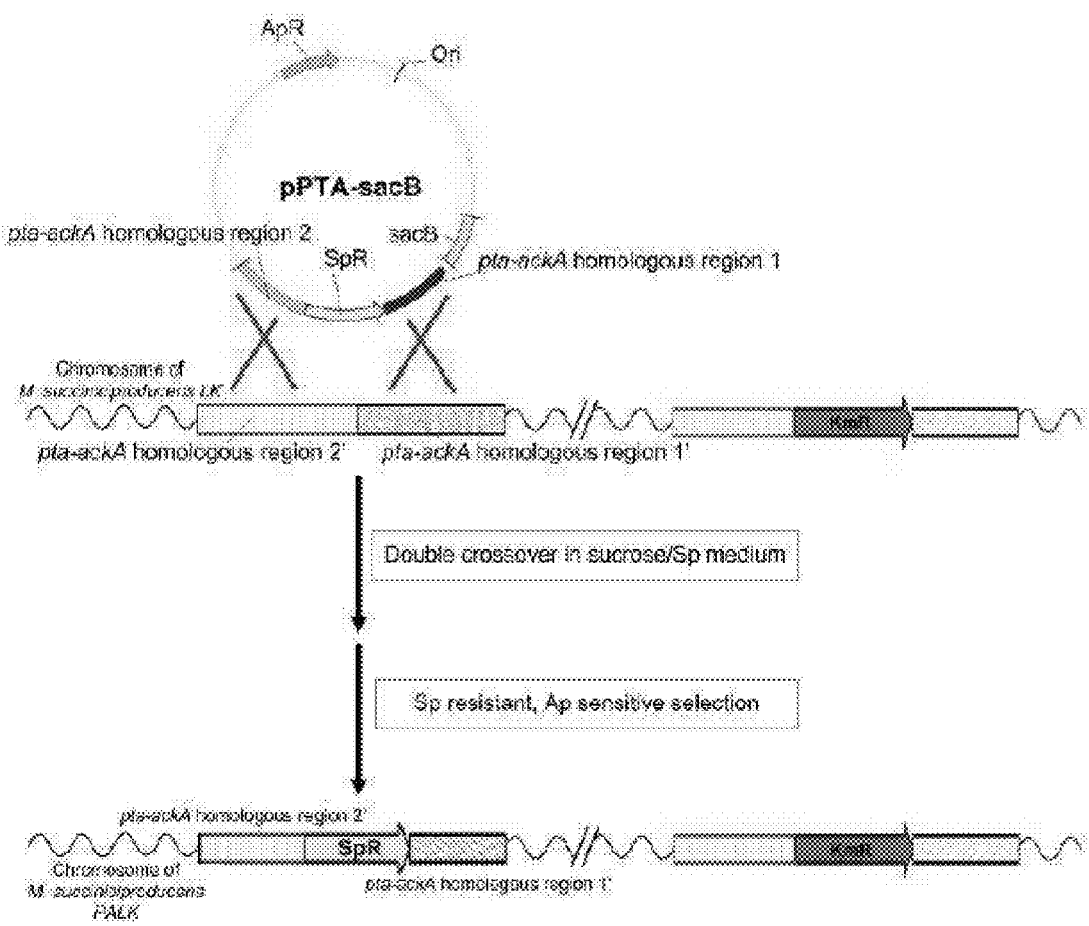
FIG. 5 shows a process of constructing a bacterial mutant (*M. succinicproducens* PALK) by disrupting pta-ackA genes in *M. succiniciproducens* LK by homologous recombination.
Figure 6:
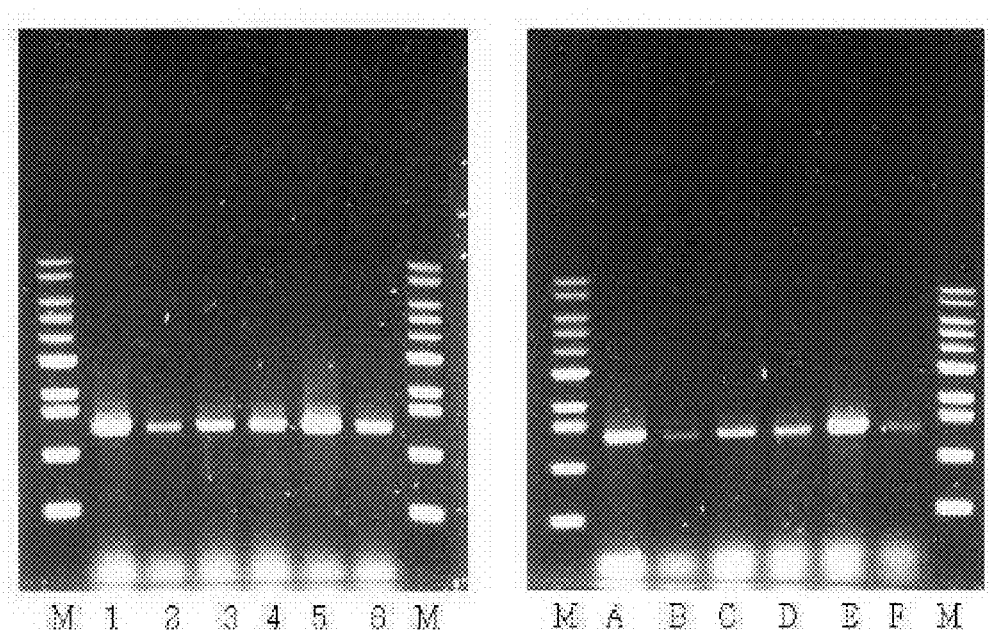
FIG. 6 is an electrophoresis photograph showing the disruption of pta-ackA in *M. succiniciproducens* PALK, wherein M represents lkb marker; lanes 1-6 represent PCR fragments (1.1 kb) using primers, PAU1 and SP1; lanes A-F represent PCR fragments (1.5 kb) using primers, SP2 and PAD2.

The products obtained in the two PCRs were subjected to gel electrophoresis to confirm the disruption of pta-ackA by their size (FIG. 6). The disruption of pta-ackA was confirmed by the fact the product resulted from the PCR using the primers of SEQ ID NO: 20 and SEQ ID NO: 21 (SP1 primer and PAU1 primer) has a size of 1.1 kb, and at the same time the product resulted from the PCR using the primers of SEQ ID NO: 22 and SEQ ID NO: 23 (SP2 primer and PAD2 primer) has a size of 1.5 kb. The position of each primer is shown in FIG. 5.

The mutant strain constructed by the disruption of pta-ackA from the genome of *M. succiniciproducens* LK as the above-described method, i.e., a mutant strain resulted from the disruption of ldhA, pta and ackA from the genome of *M. succiniciproducens*, was named "*M. succiniciproducens* PALK" and deposited under accession number "KCTC10973BP" on Jul. 26, 2006 in the Korean Collection for Type Cultures (KCTC; 52, Eoeun-dong, Yuseong-gu, Daejeon-si, Republic of Korea), Korean Research Institute of Bioscience and Biotechnology, which is an international depository authority.

Example 5

Production of Homo-Succinic Acid Using *M. succinici producens*

PALK

*M. succiniciproducens* PALK (KCTC 10973BP) constructed in Example 4 was plated on 10 ml of composition medium containing 5 g/L of glucose, and cultured in anaerobic conditions at 39° C. for 8 hours, and then again moved to 250 ml of composition medium containing 5 g/L of glucose and cultured at 39° C. At this time 50 µg/ml spectinomycin was added to the medium as an antibiotic. 250 ml of the culture broth of *M. succiniciproducens* PALK was inoculated in the bioreactor containing 2.25 L of composition medium (1 g/L of NaCl, 2 g/L of $(NH_4)_2HPO_4$, 0.02 g/L of $CaCl_2.2H_2O$, 0.2 g/L of $MgCl_2.6H_2O$, 8.709 g/L of $K_2HPO_4$, 0.5 g/L of cystein, 0.5 g/L of methionine, 0.5 g/L of alanine, 0.5 g/L of asparagines, 0.5 g/L of aspartic acid, 0.5 g/L of praline, 0.5 g/L of serine, 0.005 g/L of nicotinic acid, 0.005 g/L of Ca-pantothenate, 0.005 g/L of pyridoxine.HCl, 0.005 g/L of thiamine, 0.005 g/L of ascorbic acid, and 0.005 g/L of biotin), and the fermentation was performed under conditions of a first glucose concentration of 18.2 g/L (100 mM), a first glycerol concentration of 9.2 g/L (100 mM) at 39° C. During the fermentation, the pH of the culture was adjusted to 6.5 by using ammonia water, and 50 µg/ml spectinomycin was added to the medium as an antibiotic. In order to produce succinic acid at a high concentration, whenever glucose was completely exhausted, the glucose concentration of the culture broth was adjusted to about 18.2 g/L (100 mM) by adding concentrated glucose solution.

*M. succiniciproducens* MBEL55E (KCTC0769BP) and the succmlc acid-producing mutant strain *M. succiniciproducens* LPK7 (KCTC10626BP) were fermented to produce succinic acid in the same manner as described above.

The concentration of cells m the culture broth was measured with a spectrophotometer, and then calculated using the previously measured light absorption of spectrophotometer and the verification test for dried-cell weight. During the fermentation, samples were collected from the bioreactor regularly. The collected samples were centrifuged at 13,000 rpm for 10 minutes, and then the supernatants were used to analyze the concentrations of organic acids, glucose, and glycerol by using a High-Performance Liquid Chromatography.

Figure 7:
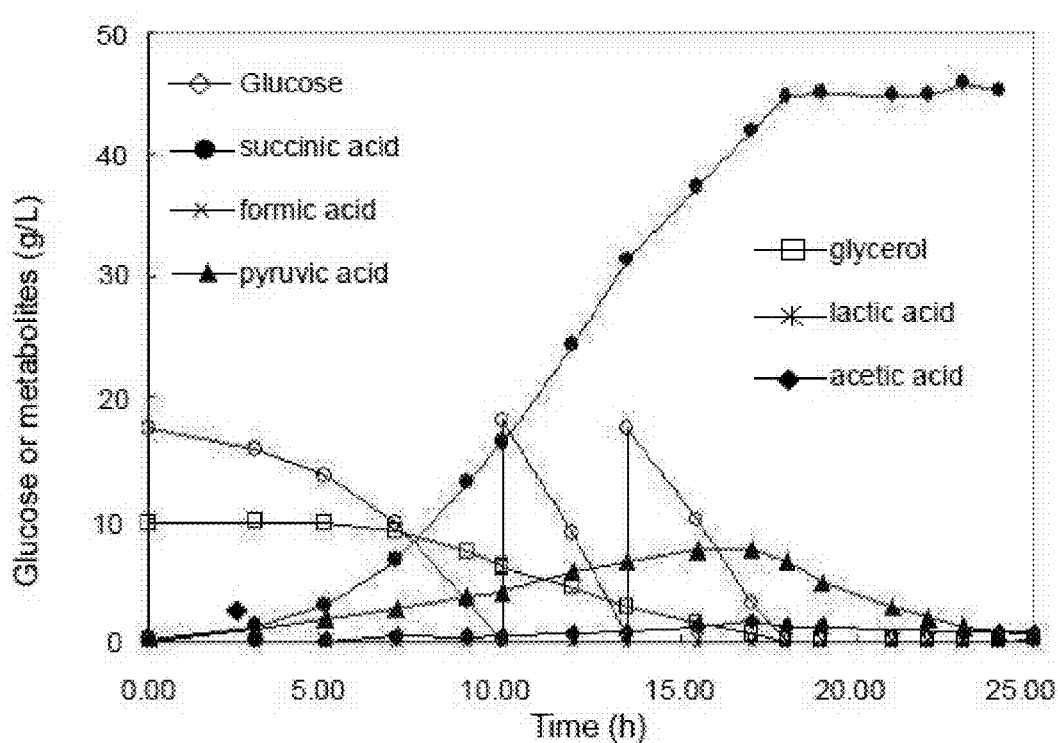
FIG. 7 shows the culture characteristics of the inventive *M. succiniciproducens* PALK in anaerobic conditions saturated with $CO_2$.

As a result, when *M. succiniciproducens* PALK (KCTC 10973BP) of the present invention was compared with *M. succiniciproducens* MBEL55E (KCTC0769BP) and *M. succiniciproducens* LPK7 (KCTC10626BP), it showed higher succinic acid productivity while producing little or no other organic acids as byproducts than *M. succiniciproducens* MBEL55E (KCTC0769BP) and *M. succiniciproducens* LPK7 (KCTC10626BP) as shown in FIG. 7 and Table 2. Although 0.45 g/L of acetic acid and 0.24 g/L of pyruvic acid were detected, it is obvious to a person skilled in the art that these amount are the minimum amounts of organic acids produced for a strain to grow and can be ignored because they were produced in amounts of less than 1 wt % compared to produced succinic acid.

TABLE 2

Succinic acid-productivity of *M succiniciproducens* PALK (KCTC10973BP)

| Strain | MBEL55E (KCTC0769BP) | LPK7 (KCTC 10626BP) | PALK (KCTC 10973BP) |
|---|---|---|---|
| Final concentration of succinic acid (g/L) | 10.49 | 13.40 | 45.79 |
| Glucose consumption (g/L) | 22.50 | 19.98 | 53.00 |
| Succinic acid yield (g succinic acid/g glucose) | 0.47 | 0.67 | 0.86 |
| Increasing rate of succinic acid compared to wild strain (MBEL55E) (%) | — | 42.55 | 82.98 |
| Final concentration of acetic acid (g/L) | 4.96 | 0.53 | 0.45 |
| Final concentration of lactic acid (g/L) | 3.47 | 0.27 | 0.00 |
| Final concentration of pyruvic acid (g/L) | 0.00 | 2.47 | 0.24 |
| Cell specific growth rate (1/h) | 0.81 | 0.30 | 0.69 |

INDUSTRIAL APPLICABILITY

As described and provided above in detail, the present invention provides the succinic acid-producing mutant microorganism having a high growth rate, which produces succinic acid at a high concentration while producing little or no other organic acids during the culture in anaerobic conditions, and the method for producing succinic acid using the same. The inventive mutant microorganism has the ability of having a high growth rate and succinic acid productivity while producing little or no organic acids, as compared to the prior strains producing succinic acid. Thus, the inventive mutant microorganism is useful to produce succinic acid for industrial use.

While the present invention has been described in detail with reference to the specific features, it will be apparent to persons skilled in the art that this description is only for a preferred embodiment and does not limit the scope of the present invention. Thus, the substantial scope of the present invention will be defined by the appended claims and equivalents thereof.

What is claimed is:

1. A mutant microorganism of a rumen bacteria, the mutant microorganism having disrupted a lactate dehydrogenase gene (ldhA), a phosphotransacetylase gene (pta), and an acetate kinase gene (ackA) while maintaining a non-disrupted pyruvate formate-lyase gene (pfl), wherein the rumen bacteria has a property of producing succinic acid, wherein the rumen bacteria are included in a genus of which *Mannheimia succiniciproducens* is included, and wherein the amount of any other organic acid produced by the mutant rumen bacterium as a byproduct in the production of succinic acid by the mutant rumen bacterium is less than 1 wt % based on the weight of succinic acid that is produced.

2. The mutant microorganism according to claim 1, wherein the mutant microorganism is a homogeneous fermentation strain producing succinic acid.

3. The mutant microorganism according to claim 1, wherein the mutant microorganism utilizes glycerol or glucose as a carbon source for producing the succinic acid.

4. The mutant microorganism according to claim 1, wherein the mutant microorganism converts phosphoenolpyruvate and pyruvate compounds into oxaloacetate and malate compounds using $CO_2$-fixing enzyme for producing the succinic acid.

* * * * *